US005457024A

United States Patent [19]
Goldbard

[11] Patent Number: 5,457,024
[45] Date of Patent: Oct. 10, 1995

[54] ISOLATION OF FETAL ERYTHROCYTES

[75] Inventor: Simon B. Goldbard, New City, N.Y.

[73] Assignee: Aprogenex, Inc., Houston, Tex.

[21] Appl. No.: 7,479

[22] Filed: Jan. 22, 1993

[51] Int. Cl.$^6$ .................. G01N 33/543; G01N 33/49; A01N 1/02
[52] U.S. Cl. .................. 435/2; 435/7.25; 435/6; 435/962; 436/17; 436/175; 436/177; 436/178; 436/518
[58] Field of Search ............. 435/2, 7.25, 962, 435/6; 436/518, 541, 17, 175, 177, 178

[56] References Cited

U.S. PATENT DOCUMENTS

| | | | |
|---|---|---|---|
| 4,185,964 | 1/1980 | Lancaster | 23/230 B |
| 4,190,535 | 2/1980 | Luderer et al. | 210/83 |
| 4,255,256 | 3/1981 | Ferrante et al. | 210/730 |
| 4,675,286 | 6/1987 | Calenoff | 435/7 |
| 4,861,705 | 8/1989 | Margel | 435/2 |
| 4,880,548 | 11/1989 | Pall et al. | 210/767 |
| 4,888,278 | 12/1989 | Singer et al. | 435/6 |
| 4,923,620 | 5/1990 | Pall | 210/767 |
| 4,925,572 | 5/1990 | Pall | 210/767 |
| 4,927,750 | 5/1990 | Dorn | 435/2 |
| 4,976,861 | 12/1990 | Pall | 210/508 |
| 5,153,117 | 10/1992 | Simons | 435/2 |
| 5,275,933 | 1/1994 | Teng et al. | 435/2 |

FOREIGN PATENT DOCUMENTS

| | | |
|---|---|---|
| WO9006509 | 6/1990 | WIPO. |
| WO9107660 | 5/1991 | WIPO. |
| WO9114768 | 10/1991 | WIPO. |
| WO9116452 | 10/1991 | WIPO. |
| WO9402646 | 2/1994 | WIPO. |

OTHER PUBLICATIONS

Miyamato, et al. Leukocyte–Poor Platelet Concentrates at the Bedside by Filtration Through Sepacell–PL Vox Sang 1989;57:164–167.

Wenz, B. Microaggregate blood filtration and the febrile transfusion reaction. A comparative Study. Transfusion. 1983;23:95–89.

Bock, M., et al. Preparation of white cell–depleted blood. Comparison of two bedside filter systems. Transfusion. 1990;30:26–29.

Steneker, I. and Biewenga, J. Histologic and immunohistochemical studies on the preparation of white cell–poor red cell concentrates: the filtration process using three different polyester filters. Transfusion. 1991;31:40–46.

Bianchi, D. W., et al. Possible Effect of Gestational Age on the Detection of Fetal Nucleated Erythrocytes in Maternal Blood. Prenatal Diagnosis. 1991;11:523–28.

Bertolini, F., et al. Comparison of Platelet Activation and Membrane Glycoprotein Ib and IIb–IIIa Expression after Filtration through Three Different Leukocyte Removal Filters. Vox. Sang. 1990;59:201–204.

Bianchi, et al. Erythroid specific antibodies enhance detection of fetal nucleated erythrocytes in maternal blood. Prenatal Diagnosis. 1993;13:293–300.

Bhat, et al. One Step separation of human fetal lymphocytes from nucleated red blood cells. Journal of Immunological Methods. 1990;131:147–49.

Bhat, et al. One Step enrichment of nucleated red blood cells. A potential application in perinatal diagnosis. Journal of Immunological Methods. 1993;158:277–80.

Price, J. O., "Prenatal diagnosis with fetal cells isolated from maternal blood by multiparameter flow cytometry", Am J Obstet Gynecol 165:1731–1737, 1991.

Gray, J. W. et al. Applications of Fluorescence In Situ Hybridization in Biological Dosimetry and Detection of Disease–Specific Chromosome Aberrations. in, New Horizons in Biological Dosimetry, 399–411 (1991).

Mueller, U. W., et al. Isolation of Fetal Trophoblast Cells from Peripheral Blood of Pregnant Women. The Lancet, 336: 197–200 (1990).

Bae–Li Hsi, "Human Trophoblast Antigens Defined by Monoclonal Antibodies", Elsevier Science Publishers BV (Biomedical Division), Reproductive Immunology 1989, L. Mettler, W. D. Billington, eds.

Bruch J. F., et al. Trophoblast–like cells sorted from peripheral maternal blood using flow cytometry: a multiparametric study involving transmission electron microscopy and fetal DNA amplification. Prenatl. Diagnosis 11: 787–798 (1991).

Covone A. E. et al. Trophoblast cells in peripheral blood from pregnant women. Lancet 336: 841–843 (1984).

Goodfellow, C. F., et al. Extraction and identification of trophoblast cells circulating in peripheral blood during pregnancy. British J. Obst. Gynecol. 89:65–68 (1982).

Hertzenberg, L. A., et al. Fetal Cells in the Blood of Pregnant Women: Detection and Enrichment by Fluorescence–activated Cell Sorting, Proc. Natl. Acad. Sci. 76: 1453–1455 (1979).

Tkachuk, D. C., et al. Clinical Applications of Fluorescence in situ Hybridization. GATA 8: 67–74 (1991).

Wachtel, S., et al. Fetal cells in the maternal circulation: isoaltion by multiparameter flow cytometry and confirmation by polymerase chain reaction. Hum. Reprod. 6: 1466–9 (1991).

Iverson, G. M., et al. Detection and isolation of fetal cells from maternal blood using the fluorescence–activated cell sorter (FACS) Prenat. Diagn. 1:61–73 (1981). Abstract Only.

Bianchi, D. W., et al. Isolation of fetal DNA from nucleated erythrocytes in maternal blood. Proc. Natl. Acad. Sci. U.S.A. 87: 3279–83 (1990).

(List continued on next page.)

Primary Examiner—Toni R. Scheiner
Assistant Examiner—Nancy Parsons
Attorney, Agent, or Firm—Elman & Fried

[57] ABSTRACT

A method for isolating nucleated fetal erythrocytes (NFEs) from a maternal blood sample by separating erythrocytes in the maternal blood sample from all other nucleated cells therein using a leukocyte depletion device; and isolating NFEs from nonnucleated maternal erythrocytes. Preferably the maternal blood is peripheral maternal blood. The isolated NFEs can then be analyzed for genetic disorders and the like, such as by in situ hybridization.

14 Claims, No Drawings

OTHER PUBLICATIONS

Bianchi, D. W., et al. Use of dual PCR to quantify fetal cells isolated from maternal blood. Am. J. Hum. Gen. 55: 1619 (1994).

Ganshirt–Ahlert, D., et al. Magnetic cell sorting and the transferrin receptor as a potential means of prenatal diagnosis from maternal blood. A. J. Obstet. Gunecol. 166: 1350–5 (1992).

Holzgreve, W., et al. Fetal Cells in the Maternal Circulation. J. Reprod. Med. 37: 410–8 (1992).

Ganshirt–Ahlert, D., et al. Detection of Fetal Trisomies 21 and 18 From Maternal Blood Using Triple Gradient and Magnetic Cell Sorting. Am. J. Reprod. Immunol. 30: 194–201 (1993).

Cheuh, J., et al. The search for fetal cells in the maternal circulation. J. Perinat. Med. 19: 411–20 (1991).

Komlos, L., et al. Expression of Transferrin Receptor on Human Maternal and Neonatal Peripheral Blood Lymphocytes. Am J. Reprod. Immunol. 26: 124–8 (1991).

Camaschella, C., et al. Prenatal Diagnosis of Fetal Hemoglobin Lepore–Boston Disease on Maternal Peripheral Blood. Blood 75: 2102–6 (1990).

ISOLATION OF FETAL ERYTHROCYTES

BACKGROUND OF THE INVENTION

The invention relates to a procedure for the isolation and enrichment of nucleated fetal erythrocytes (hereinafter NFEs) from maternal blood during the early stages of pregnancy, particularly for subsequent prenatal diagnosis such as by in situ hybridization.

Several devices and methods have been developed for separation of blood components, particularly for separation of red blood cells, platelets, leukocytes and plasma from one another. See, for example, U.S. Pat. Nos. 4,880,548, 4,923, 620 and 4,925,572 incorporated herein by reference. These methods and devices have been directed at separation of whole blood components for blood banking of packed erythrocytes or packed platelets from which fibrinogen and/or fibrin gels, microaggregates, and leukocytes have been removed, transfusion or therapeutic, particularly emergency, administration of individual concentrated components usually in relatively large volumes, i.e., one or more units (450 ml. each).

The number of NFEs present in maternal blood is very low (estimates are from 1 in 10,000 to 1 in 1,000,000). The current state of the art does not permit the isolation of these cells mainly because of the presence of large numbers of maternal cells.

SUMMARY OF THE INVENTION

The invention provides a method used to separate NFEs from the peripheral blood of women in their first or second trimester of pregnancy. Since this constitutes a non-invasive procedure with no danger to either mother or fetus, the test can be used for all pregnant women regardless of age and risk factors. Blood collection is done at the doctor's office, clinic or elsewhere and cell isolation and analysis can be performed in similar facilities and in clinical genetics laboratories. The NFE isolation method of the invention is used to provide samples of isolated fetal erythrocytes for analysis by technologies like in situ hybridization for the prenatal diagnosis of genetic disorders.

Accordingly, the method provided by the invention is one for isolating NFEs from maternal blood by separating NFEs in a sample of maternal blood from all other nucleated cells therein; and isolating NFEs from nonnucleated maternal erythrocytes. Preferably the maternal blood sample is from peripheral maternal blood. The isolated NFEs can be analyzed for genetic disorders and the like such as by in situ hybridization.

PREFERRED EMBODIMENTS

Thus, in a principal aspect, the invention relates to a method for isolating NFEs from a sample of maternal blood. This method comprises separating NEFs in a sample of maternal blood from all other nucleated cells therein; and isolating the NFEs from nonnucleated maternal erythrocytes. Preferably, the sample is of peripheral maternal blood and is collected in amounts of about 5 to 50 ml of maternal blood.

In a first aspect, the erythrocytes in the maternal blood sample are separated from other nucleated cells by passing the whole blood sample through a leukocyte depletion device and collecting the erythrocytes that have passed through the filter. Surprisingly, the nucleated fetal erythrocytes pass through with the nonnucleated maternal erythrocytes rather than being retained with the nucleated leukocytes. This leukocyte depletion device is preferably a small version of the type made and sold by Pall Corporation, Glen Cove, N.Y. and described in detail in U.S. Pat No. 4,925,572.

When a liquid is brought into contact with the upstream surface of a porous medium and a small pressure differential is applied, flow into and through the porous medium may or may not occur. A condition in which no flow occurs is that in which the liquid does not wet the material of which the porous structure is made. A series of liquids can be prepared, each with a surface tension of about 3 dynes/cm higher compared with the one preceding. A drop of each may then be placed on a porous surface and observed to determine whether it is absorbed quickly, or remains on the surface.

Similar behavior is observed for porous media made using other synthetic resins, with the wet-unwet values dependent principally on the surface characteristics of the material from which the porous medium is made, and secondarily, on the pore size characteristics of the porous medium. For example, fibrous polyesters (specifically polybutylene terephthalate (hereinafter "PBT") sheets) which have pore diameters less than about twenty micrometers were wetted by a liquid with a surface tension of 50 dynes/cm, but were not wetted by a liquid with a surface tension of 54 dynes/cm.

In order to characterize this behavior of a porous medium, the term "critical wetting surface tension" (hereinafter "CWST") has been defined as described below. The CWST of a porous medium may be determined by individually applying to its surface, preferably dropwise, a series of liquids with surface tensions varying by 2 to 4 dynes/cm, and observing the absorption or nonabsorption of each liquid. The CWST of a porous medium, in units of dynes/cm, is deemed as the mean value of the surface tension of the liquid which is absorbed and that of a liquid of neighboring surface tension which is not absorbed.

In measuring CWST, a series of standard liquids for testing are prepared with surface tensions varying in a sequential manner by 2 to 4 dynes/cm. Wetting is defined as absorption into or obvious wetting of the porous medium by at least 90% of the drops of a given standard within 10 minutes. Non-wetting is defined by non-absorption or non-wetting of at least 90% of the drops of a given standard in 10 minutes. Testing is continued using liquids of successively higher or lower surface tension, until a pair has been identified, one wetting and one non-wetting, which are the most closely spaced in surface tension. The CWST is then within that range and, for convenience, the average of the two surface tensions is used as a single number to specify the CWST. Appropriate solutions with varying surface tensions are reported in U.S. Pat. No. 4,925,572.

In whole blood, the red cells are suspended in blood plasma, which has a surface tension of 73 dynes/cm. Hence, if whole blood is placed in contact with a porous medium, spontaneous wetting will occur if the porous medium has a CWST of 73 dynes/cm or higher.

One embodiment of the invention used a device for the depletion of the leukocyte content of a blood sample comprising at least first, second, and third preformed porous elements with the second element interposed between the first and third elements. Each successive element has a smaller pore diameter than that preceding it. The first element is for removing gels, the second element is for removing microaggregates, and the third element is for removing leukocytes. This embodiment of the leukocyte depletion device has a third element which has a pore diameter in the range from about 4 to about 8 micrometers, preferably in the range of from about 4 to about 5.5 micrometers.

In another embodiment, the device has a first element which comprises a needled fibrous structure, and can be hot compressed to a controlled thickness. The average pore diameter of this first element can be such that, when prewetted by isopropyl alcohol, a differential pressure of 4 to 7 cm of water column induces air flow through it at the rate of 0.5 cm/second.

Also, the device can include at least two interposed or laminated elements of porous media which stepwise span in approximate geometric progression the pore diameter range of from about 25 to about 10 micrometers.

For example, the device can include at least two interposed elements of porous media which have progressively stepwise decreasing pore diameters spanning the range from about 25 to about 10 micrometers, or can include a single element in which the pore diameter varies stepwise from about 25 micrometers to the range of from about 10 to about 15 micrometers.

One or more elements of the device is preferably treated with a surfactant. The surfactant induces a surface tension of about 75 to 45 dynes/cm in a blood sample. As a further alternative, at least one element can be surface modified by an energy source while in contact with a monomer containing at least one hydroxyl moiety and one moiety capable of activation by an energy source, together with a monomer containing at least one hydrophobic moiety and one moiety capable of activation by an energy source.

Most particularly, the device has an element in which the means for removing leukocytes includes a filtration means. Preferably, this element is preformed of synthetic fibers whose surface has a modified CWST in excess of 53–63 dynes/cm. These fibers can be surface modified by exposure to an energy source while in contact with monomers as described above.

The invention can additionally use a device for depletion of leukocytes from a blood product comprising at least one element in which a fibrous medium has been radiation grafted to obtain a critical wetting surface tension in excess of 53 dynes/cm and thereafter hot compressed to form a non-friable coherent body. This device can have a CWST in the range of about 55 to 75 dynes/cm, and can also have the fibrous surface modified by exposure to an energy source while in contact with monomers as described above.

The invention can also use a device for leukocyte depletion comprising a preformed element of synthetic fibers modified to a CWST in the range of about 55 to 75 dynes/cm, and can also have the fibrous surface modified by exposure to an energy source while in contact with monomers as described above.

The invention particularly uses a device for the leukocyte depletion of a blood sample comprising a housing including an inlet and an outlet and defining a fluid flow path between the inlet and the outlet, an upstream porous element for removing gels, at least one intermediate porous element for removing microaggregates, and a downstream porous element for removing leukocytes, the elements being secured within the housing by an interference fit.

In another aspect, the nucleated fetal erythrocytes are isolated from nonnucleated maternal erythrocytes by centrifugal separation through a pore gradient material. Usually about 90%, i.e., 4.5 to 45 ml of the fluid volume of the sample, now freed of leukocytes, passes through the leukocyte depletion device, while the small remaining amount of fluid volume is retained in the device. The material to be centrifugally separated is preferably diluted 3–7 fold in a physiological fluid, such as phosphate buffered saline (hereinafter "PBS"). Preferably the gradient is of a polysaccharide, for example, a 4–20% sucrose gradient. Examples of such pore gradient materials include Ficoll and Percoll gradient materials available from SIGMA Chemical Co., St. Louis, Mo.

Another useful method for isolating the nucleated from nonnucleated erythrocytes comprises lysing the nonnucleated maternal erythrocytes, such as with ammonium chloride. The erythrocyte-containing fluid volume is mixed with ammonium chloride, usually about 0.1–0.2M aqueous concentration in about a 1:4 (v/v) ratio.

The method of the invention for isolating the nucleated erythrocytes from nonnucleated maternal erythrocytes can be supplemented by the known method of reacting erythrocytes with solid phase bound antibody specifically bindable with the nucleated erythrocytes and separating the unbound nonnucleated erythrocytes therefrom. This would be performed subsequent to the fetal erythrocyte isolation method of the invention. A suitable antibody can be of any of the types of polyclonal, monoclonal, single chain, $Fab_2$ region fragments or other variants that retain the desired specificity. The antibody is bound directly or through any typical linkage group to a solid phase of known type including slides, beads, microparticles or microcapsules, magnetic beads or the like. One preferred specificity or ligand for such an antibody is the transferring receptor. Antibodies to the transferring receptor can be obtained from Becton-Dickinson, Piscataway, N.J.

Another aspect of the invention provides for assaying nucleic acid in nucleated fetal erythrocytes by methods known to those of skill in the art. This method includes separating NFEs in a sample of maternal blood from all other nucleated cells therein; isolating the NFEs from nonnucleated maternal erythrocytes; and assaying by methods known to those of skill in the art nucleic acid associated with the NFEs so isolated.

In a preferred embodiment of this aspect the nucleic acid assayed are in nucleated fetal erythrocytes having substantially intact membranes and the nucleic acids are intact fetal chromosomes or fragments thereof.

EXAMPLE 1

Nucleated Fetal Erythrocyte Isolation

Fifty (50) ml of pooled umbilical cord blood were filtered using a leukocyte removal filter (RC 50 from Pall Biomedical Products Corporation, Glen Cove, N.Y.). An empty 60 ml syringe barrel was connected to the filter by a short length of tubing and the blood subsequently passed through the RC 50 filter. The collected fraction containing the erythrocytes (26 ml) was diluted in five times its volume of PBS and overlaid on a Histopaque 1.077 gradient (SIGMA, St. Louis, Mo.). The gradient was centrifuged for 40 minutes at 300 g and the cells at the interface were removed, washed once in PBS, and centrifuged to form pellets. The pellets were combined, resuspended in PBS, and the cells were placed onto slides by centrifugation using a cytocentrifuge.

The slides were fixed in ethanol/methanol (3:1) for two minutes, stained with Giemsa stain, and observed under the microscope. Nucleated erythrocytes were visually scored and counted. The only nucleated cells seen were nucleated erythrocytes. From the counts it was calculated that approximately 5000 nucleated erythrocytes were recovered.

What is claimed is:

1. A method for isolating nucleated fetal erythrocytes from maternal blood which comprises:

separating erythrocytes in a sample of maternal blood from all nucleated non-erythrocyte cells therein by a technique which comprises passing the blood through a leukocyte depletion device and collecting the erythrocytes that have passed through the device; and from the erythrocytes so collected, isolating the nucleated fetal erythrocytes from nonnucleated maternal erythrocytes.

2. The method of claim 1 wherein the sample of maternal blood is peripheral maternal blood.

3. The method of claim 2 wherein the sample comprises about 5 to 50 ml of peripheral maternal blood.

4. The method of claim 1 wherein isolating the nucleated fetal erythrocytes from nonnucleated maternal erythrocytes comprises centrifugal separation through a pore gradient material.

5. The method of claim 1 wherein isolating the nucleated fetal erythrocytes from nonnucleated maternal erythrocytes comprises lysing the nonnucleated erythrocytes.

6. The method of claim 5 wherein the nonnucleated maternal erythrocytes are lysed with ammonium chloride.

7. The method of claim 1 wherein isolating the nucleated fetal erythroytes from nonnucleated maternal erythrocytes comprises reacting the erythrocytes with solid phase-bound antibody which specifically binds the nucleated fetal erythrocytes and separating the unbound nonnucleated erythrocytes therefrom.

8. The method of claim 3 wherein isolating the nucleated fetal erthrocytes from nonnucleated maternal erythrocytes comprises centrifugal separation through a pore gradient material.

9. The method of claim 8 which further comprises collecting and concentrating the nucleated fetal erythrocytes so isolated.

10. The method of claim 1 wherein the leukocyte depletion device comprises a housing including an inlet and an outlet and defining a fluid flow path between the inlet and the outlet, an upstream porous element for removing gels, at least one intermediate porous element for removing microaggregates, and a downstream porous element for removing leukocytes.

11. The method of claim 10 wherein the downstream porous element has a diameter in the range of from about 4 to about 8 micrometers.

12. The method of claim 1 wherein the leukocyte depletion device comprises a preformed element of synthetic fibers modified to a critical wetting surface tension in the range of about 55 to 75 dynes/cm.

13. The method of claim 12 wherein the preformed element has been surface modified by exposure to an energy source while in contact with a monomer containing at least one hydroxyl moiety and one moiety capable of activation by the energy source and with a monomer containing at least one hydrophobic moiety and one moiety capable of activation by the energy source.

14. The method of claim 1 wherein the leukocyte depletion device comprises an element which has been treated with a surfactant so as to induce a surface tension of about 75 to 45 dynes/cm in a blood sample.

* * * * *